(12) United States Patent
Kiczek, Sr. et al.

(10) Patent No.: US 6,258,343 B1
(45) Date of Patent: Jul. 10, 2001

(54) METHOD FOR ENCAPSULATING REACTIVE DENTAL AGENTS

(75) Inventors: Alexander P. Kiczek, Sr., Middletown; Mike Wong, Plainsboro, both of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/639,287

(22) Filed: Aug. 15, 2000

(51) Int. Cl.⁷ ........................................ A61K 7/18
(52) U.S. Cl. .................. 424/52; 424/489; 424/490; 424/494; 424/495
(58) Field of Search ............. 424/49–58, 489–490, 424/494–495

(56) References Cited

U.S. PATENT DOCUMENTS

| | | | |
|---|---|---|---|
| 3,929,988 | * 12/1975 | Barth | 424/54 |
| 3,957,964 | * 5/1976 | Grimm | 424/49 |
| 4,220,552 | * 9/1980 | Hitchcock | 424/52 |
| 4,552,679 | * 11/1985 | Schobel | 252/90 |
| 4,568,560 | * 2/1986 | Schobel | 424/49 |
| 4,777,089 | * 10/1988 | Tarizawa | 424/56 |
| 4,923,683 | * 5/1990 | Sakuma | 424/52 |
| 5,362,478 | * 11/1994 | Desai et al. | 424/9 |
| 5,423,337 | * 6/1995 | Ahlert et al. | 132/321 |
| 5,780,055 | * 7/1998 | Habib et al. | 424/489 |
| 5,976,507 | * 11/1999 | Wong et al. | 424/52 |
| 6,159,449 | * 12/2000 | Winston et al. | 424/52 |

* cited by examiner

*Primary Examiner*—Shep K. Rose
(74) *Attorney, Agent, or Firm*—Paul Shapiro

(57) ABSTRACT

A method for encapsulating a water soluble reactive agent in an alkyl cellulosic polymer to provide an encapsulated product from which leaching of the reactive agent into an aqueous dentifrice containing another compound reactive with the agent is prevented or controlled, said method comprising the steps of (a) uniformly dispersing the reactive agent in the alkyl cellulose and a solvent for the polymer to form a paste;
(b) casting the paste onto a sheet forming substrate;
(c) grinding and subdividing the sheet having the reactive agent encased therein into particles of a predetermined size;
(d) washing the particles with water to remove any encased agent exposed by the grinding; and,
(e) drying the particles of encapsulated reactive agent.

6 Claims, No Drawings

METHOD FOR ENCAPSULATING REACTIVE DENTAL AGENTS

BACKGROUND OF THE INVENTION

1. Field of the Invention

The invention is directed to a solvent casting method for encapsulating water soluble reactive agents used in aqueous dentifrice compositions to prevent premature leakage into the dentifrice of the agents so as avoid interaction with other dentifrice ingredients.

2. The Prior Art

It has long been known to include fluoride containing compounds in dentifrices as anticaries agents, and it has been established that these compounds are effective to reduce the incidence of dental caries. Fluoride compounds which are deemed to be the most effective are sodium fluoride, sodium monoflurophosphate and stannous fluoride. The fluoride compounds are effective mainly due to the fluoride ions which improve the acid resistance of tooth enamel and accelerate recalcification of decayed teeth in their early stage when the decalcification has proceeded only slightly. The effect of improving the acid resistance of the enamel is believed to be due to the fact that the fluoride ions are incorporated into a crystal lattice of hydroxyapatite which is the main constituent of tooth enamel or, in other words, fluoride ions partially fluoridate hydroxyapatite and simultaneously repair the lattice irregularities.

The effectiveness of fluoride treatment in providing acid resistance is dependent upon the amount of fluoride ion which is available for deposition on the enamel being treated. It is, therefore, desirable to formulate dentifrice compositions which provide maximum fluoride ion availability in brushing solutions formed using the dentifrice.

It is known to the art, e.g., U.S. Pat. No. 5,045,305, that an effective way of depositing fluoride on teeth is to use a two-component rinse composition to deposit freshly precipitated calcium fluoride on teeth in which one rinse solution contains $CaCl_2$ and the other contains fluoride ions in the form of NaF, the separate solutions being admixed immediately prior to introduction in the mouth, to effect interaction and rapid precipitation of $CaF_2$.

U.S. Pat. No. 5,145,668 discloses a method of fluoridating teeth wherein there is mixed in the mouth a first solution containing a soluble calcium salt such as $CaCl_2$ contained in a non-reactive vehicle and a second component containing a fluoride compound such as sodium fluorosilicate ($Na_2SiF_6$) contained in a non-reactive vehicle, the mixing of the components resulting in the precipitation of calcium fluoride and its deposition on tooth surfaces.

Although the methods disclosed in U.S. Pat. No. 5,045,305 and U.S. Pat. No. 5,145,668 are effective means to achieve fluoridation, the separate solutions containing calcium and fluoride salts must be mixed daily which is a time consuming daily chore. As a result, it is very difficult for the potential beneficiaries of such therapy to faithfully adhere to the regimen. However, simply combining the calcium and fluoride salts into a single dentifrice formulation will not provide an effective means for fluoridation as the presence of the calcium salt removes soluble ionic fluoride from the dentifrice by forming insoluble and inactive calcium fluoride ($CaF_2$) thereby reducing the anticariogenic effectiveness of the fluoride dentifrice.

Thus, there is a clear need to formulate a dentifrice product such as a toothpaste or gel utilizing a fluoride compound or other active compound wherein the ingredients used to prepare the dentifrice vehicle do not interact with each other such as in the aforementioned inactivation of fluoride ion so that optimum uptake of fluoride is accomplished when the dentifrice is applied to the teeth. Moreover, it is desirable to include water soluble reactive compounds such as calcium and fluoride salts in a single highly stable dentifrice form which is susceptible to conventional packaging and dispensing systems and which can be readily and effectively used by the consumer.

The dentifrice art discloses several means to isolate active ingredients from interaction with other ingredients present in the dentifrice. For example, U.S. Pat. Nos. 3,957,964; 3,929,988; 4,071,614; 4,220,552; 4,348,378; and, 4,376,762 disclose aqueous dentifrices containing ingredients such as flavors and dyes whereby such ingredients are encapsulated in rupturable, water-insoluble capsules so that the flavors and dyes are maintained substantially separate from other dentifrice ingredients during manufacture and storage, while subsequently being released when the dentifrice containing the encapsulated ingredients are applied topically to tooth surfaces, the mechanical agitation with a toothbrush rupturing the encapsulating shell whereby the encapsulated ingredient is released to the tooth surface. Materials from which the encapsulating shell is formed are diverse and include synthetic organic plastic materials such as phenol formaldehydes, vinyl chloride polymers, polyethylene, polypropylene, polyurethanes, ABS resins, waxes and cellulosic materials such as ethyl cellulose, butyl cellulose and nitrocellulose.

Although the water insoluble encapsulant materials of the prior art are effective to some degree to prevent interaction between water soluble reactive dentifrice ingredients, such materials were found to be inadequate to fully prevent interaction due to premature leakage of soluble reactive salts from the encapsulating material whereby, when encapsulated calcium salts were present in fluoride dentifrices, there resulted a significant loss of ionic fluoride and reduced levels of soluble fluoride availability in the dentifrice compositions stored for prolonged period of time.

U.S. Pat. No. 5,976,507 discloses one solution to the leakage problem encountered with water soluble reactive agents such as water soluble calcium salts encapsulated in alkyl cellulosic materials wherein the dentifrice in which the encapsulated reactive agent is present is prepared using an aqueous vehicle containing fluoride salts. In accordance with U.S. Pat. No. 5,976,507 one of the reactive agents is encapsulated by a spraying drying process wherein a water-insoluble, pressure rupturable shell is formed from a substantially water impermeable plasticized alkyl cellulose polymer which shell is rupturable during tooth brushing causing the encapsulated material to be released for interaction with the other active compounds present in the dentifrice composition. Although the plasticized alkyl cellulose was found effective in preventing of water soluble salts into the dentifrice, the encapsulated product was found to be too costly for wide spread commercial acceptance.

SUMMARY OF THE INVENTION

In accordance with the present invention there is provided a method for encasement of a water soluble reactive agent such as a calcium salt, in an alkyl cellulosic polymer matrix which prevents or controls leaking of the reactive agent from the matrix, the matrix not undergoing rupture or disintegration during processing of the dentifrice.

In the method of the present invention the reactive agent to be encased is uniformly dispersed with the alkyl cellulosic polymer in a solvent for the polymer to form a viscous, semi-solid homogeneous paste constituting a castable mass of a homogeneous matrix with the reactive agent distributed therethrough, which mass is cast onto a sheet forming substrate to form a sheet of reactive agent encased in the alkyl cellulosic polymer matrix. The sheet is dried to remove the solvent, stripped from the substrate and pulverized to subdivide the matrix into particles of encased reactive agent of a predetermined size. Thereafter the particles are washed with water or other solvent for the reactive agent to remove any non-encased agent, the alkyl cellulosic polymer encased particles being of sufficient strength to maintain particle integrity during the processing of the dentifrice composition into which the particles are incorporated but subject to softening by the dentifrice ingredients during storage so that the matrix is readily disintegrated during toothbrushing whereby the reactive agent is released for interaction with other active compounds present in the dentifrice composition.

As will hereinafter be demonstrated, unexpectedly, the solvent casting method of the present invention to prepare encapsulated water soluble reactive agent particles is effective to prevent leaking of the agent from the alkyl cellulosic polymer encapsulant without the use of a spray drying process or the presence of a plasticizer as required in U.S. Pat. No. 5,976,507, thereby substantially reducing the cost of manufacture of the encapsulated reactive agent particles and thereby promoting acceptance by the consumer.

DESCRIPTION OF THE PREFERRED EMBODIMENTS

In the present invention, encapsulated water soluble reactive agents such as soluble calcium and fluoride salts, such as calcium chloride, calcium acetate, sodium fluoride, sodium monofluorophosphate or other compounds such as peroxide compounds including calcium peroxide, urea peroxide and hydrogen peroxide, potassium salts including chloride, stannate, and nitrate, manganese, copper, iron and zinc salts including chloride, gluconate, citrate, acetate which release reactive ions are isolated from the surrounding aqueous dentifrice environment by a water impermeable alkyl cellulosic polymer coating which subsequently releases the reactive agent, that is, ruptures, in response to forces exerted during toothbrushing.

In the practice of the present invention, the reactive agent comprises about 40 to about 80% by weight of the particles and the encapsulating alkyl cellulosic polymer comprises about 20 to about 60% by weight of the particles and preferably about 50 to about 70% by weight of the reactive agent and about 30 to about 50% by weight of the cellulosic polymer.

The encapsulation material used to prepare the water impermeable particles of the present invention is a substantially water-insoluble film forming alkyl cellulosic polymer material. The term "alkyl cellulosic polymer" includes within its meaning methyl cellulose, ethyl cellulose, hydroxyethylcellulose, and hydropropyl methyl cellulose.

It is a feature of the present invention that substantially water impermeable, pressure rupturable encasement of reactive agent ingredients is accomplished with an alkyl cellulosic polymer material which does not require modification by a plasticizer.

In the method of the present invention a solution of alkyl cellulosic polymer is mixed with a solvent for the alkyl cellulosic polymer preferably a monohydric alcohol such as ethanol, in a conventional mixing apparatus such as a Ross mixer with the water soluble reactive agent to form a viscous paste. The paste is then delivered to a sheet formed therefrom on a heated sheet forming carrier substrate.

The carrier substrate is heated to a temperature between about 100° to 120° C. Sufficient solvent is removed from the sheet within about a minute and dispelled to a recovery unit whereby the dried sheet is rendered somewhat brittle. The sheet is then physically broken into small particles by grinding, using equipment such as a mixed media grinder (Sweco™ grinder). The particles are then subject to one or more water washing steps at 18° to 65° C. to remove any encased reactive agent which has been subsequently exposed by the grinding operation.

In the preferred method of the present invention, ethyl cellulose is used as an encapsulating material and an organic solvent for ethyl cellulose such as ethanol is placed in a mixing apparatus. A reactive agent such as calcium acetate and the ethyl cellulose are added to the ethanol in the mixer. Mixing is a batch operation carried out with agitation provided by a high shear mixer (Ross™). The preferred composition of ingredients charged to the mixer is about 35% by weight of a reactive agent such as calcium acetate, about 15% ethyl cellulose and about 50% by weight ethanol. After the ingredients have been added to the solvent, the mixer is closed and sealed to prevent loss of solvent. When ethyl alcohol is used as the solvent, the mixing is performed at ambient (22° C.) temperature. Preferably, mixing continues until the viscosity of the mixture assumes a paste form.

Thereafter, the mixture is pumped by suitable means to a casting surface. The casting surface, or substrate, can be a casting drum or endless belt of highly polished stainless steel, copper or silicone rubber. In a preferred embodiment, the casting surface is a double drum dryer or single drum dryer with an applicator roll which rotates at a speed of about 1.5 ft./min. providing a moving casting surface in a casting chamber provided with a solvent vapor recovery system which is closed to the environment.

The casting surface is provided with a heating zone and a cooling. Generally, the sheet is heated in the casting surface at 800 to 120° C. which causes the solvent to vaporize, removing the solvent from the paste deposited on casting belt to form the sheet.

The dried sheet is cooled and then stripped from the casting surface, passed into a mixed media grinder and pulverized into particles which are screened to pass through a 30 mesh screen but retained on a 100 mesh screen to a particle size referred to as −30+100 mesh. Thereafter the particles are washed with water and then dried in an air stream at 150° to 200° C. whereby any reactive agent which has been exposed by the grinding action is removed.

The dentifrice composition in which the encapsulated reactive agent particles are incorporated is prepared in the form of a semi-solid product of desired consistency which is extrudable from a pump or collapsible tube. In general, the liquids that form the dentifrice vehicle will comprise water, in an amount ranging from about 5 to about 30% by weight and preferably about 5 to about 20% by weight and a humectant such as glycerin, sorbitol polyethylene glycol or a mixture thereof in an amount greater than about 35% by weight and preferably about 50 to about 70% by weight.

In the preparation of dentifrices which are to be used for the fluoridation of teeth, agents which interact with fluoride ions which are included in the dentifrice composition of the present invention are maintained physically isolated from the fluoride ingredient by their encapsulation in a coating of the alkyl cellulosic polymer. To obtain freshly precipitated calcium fluoride upon brushing teeth with the dentifrice composition, there is included in the dentifrice composition a water soluble calcium salt such as calcium chloride, calcium acetate, calcium butylate, calcium citrate, calcium lactate, calcium salicylate, and other non-toxic salts of calcium and inorganic or organic acids which are soluble in an aqueous media and are present in the dentifrice at a level required for substantial interaction with the fluoride compound to deposit $CaF_2$ during the time the dentifrice is applied to the teeth and brushed.

Particles of the encapsulated calcium ion releasable salt are incorporated in the dentifrice composition of the present invention at a concentration of about 0.1% to about 5% by weight and preferably at about 0.15 to about 1.5% by weight.

Suitable fluoride salts useful as fluoridation agents include alkali metal fluoride salts such as sodium fluoride, sodium monofluorophosphate and tin salts such as stannous fluoride. The fluoride salt is incorporated in the dentifrice composition at a concentration of about 0.1 to about 1% by weight, and preferably at about 0.25 to about 0.5% by weight. At these preferred concentrations, about 500 ppm to about 2200 ppm, fluoride ion will be available to teeth when the dentifrice composition is applied to the teeth.

Surfactants are used in the compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate and higher fatty acid esters of 1,2-dihydroxy propane sulfonate. The surfactant is typically present in the dentifrice compositions of the present invention in an amount of about 0.3 to about 5% by weight, preferably about 0.5 to about 2% by weight.

Thickening agents commonly used as dentifrice thickening agents such as guar gum, carboxymethyl cellulose and polyoxyethylene polyoxypropylene glycol block copolymers and xanthan gum are used at a concentration of about 0.5 to about 2% in the preparation of the dentifrice composition of the present invention which amount is sufficient to form of a semi-solid, extrudable, shape retaining product.

An abrasive is generally included in the dentifrice composition of the present invention at a concentration of about 10 to about 60% by weight and preferably at a concentration of about 15 to about 55% by weight. Soluble abrasives include precipitated amorphous hydrated silica, such as Sorbosil AC-35 marketed by Crosfield Chemicals, or Zeodent 115 from J.M. Huber Company, sodium metaphosphate, potassium metaphosphate, tricalcium phosphate, calcium phosphate dihydrate, anhydrous dicalcium phosphate, calcium pyrophosphate, sodium bicarbonate, calcium carbonate and calcined alumina.

Abrasives such as calcium carbonate and dicalcium phosphate (anhydrous and/or dihydrate) may be encapsulated in accordance with the method of the present invention for although substantially water insoluble, will nonetheless release amounts of water soluble calcium ion in sufficient amounts to interact and thereby inactivate reactive agents such as fluoride ion present in the dentifrice.

In addition to abrasive materials being incompatible with fluoride salts, it has been further determined that water soluble pyrophosphate salts, normally included in dentifrice compositions as antitartar agents, have also been determined to inactivate fluoride ion so it is desirable that these salts be encapsulated in accordance with the practice of the present invention. Exemplary antitartar pyrophosphate salts include dialkali or tetraalkali metal pyrophosphate salts such as $Na_4P_2O_7$, $K_4P_2O_7$, $Na_4K_2P_2O_7$, $Na_4H_2P_2O_7$ and $K_2H_2P_2O_7$ long chain polyphosphates such as sodium hexametaphosphate, sodium tripolyphosphate and cyclic phosphates such as sodium trimetaphosphate. These salts are included in the dentifrice composition of the present invention at a concentration of about 1 to about 7% by weight.

Synthetic anionic polycarboxylates may also be used in the dentifrice compositions of the present invention to enhance the efficacy of other active agents present in the dentifrice such as antibacterial agents and the antitartar pyrophosphate salts. Such anionic polycarboxylates are generally employed in the form of their free acids or preferably partially or more preferably fully neutralized water soluble alkali metal, e.g., potassium and preferably sodium or ammonium salts. Preferred polycarboxylate compounds are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000 most preferably about 30,000 to about 500,000. These copolymers are commercially available, for example, under the trade designation, as Gantrez, e.g. AN 139 (M.W. 500,000), AN 119 (M.W. 250,000); and preferably S-97 Pharmaceutical Grade (M.W. 70,000). The synthetic anionic carboxylates may be included in the dentifrice composition of the present invention at a concentration of about 0.5 to about 5% by weight.

The dentifrice composition of the present invention may also contain a flavoring agent. The flavoring agent is incorporated in the dentifrice composition at a concentration of about 0.1 to about 5% by weight and preferably about 0.5 to about 1.5% by weight. Flavoring agents which are used in the practice of the present invention include essential oils as well as various flavoring aldehydes, esters, alcohols, and similar materials. Examples of the essential oils include oils of spearmint, peppermint, wintergreen, sassafras clove, sage, eucalyptus, marjoram, cinnamon, lemon, lime, grapefruit, and orange. Of these, the most commonly employed are the oils of peppermint and spearmint.

Various other materials may be incorporated in the dentifrice compositions of this invention, including antibacterial agents such as Triclosan, chlorhexidine, desensitizers such as potassium nitrate, and potassium citrate, whitening agents such as hydrogen peroxide, calcium peroxide and urea peroxide, preservatives, silicones, and chlorophyll compounds. These adjuvants, when present, may also be encapsulated when they are incorporated in the dentifrice composition in amounts which are reactive with other dentifrice ingredients such as fluoride salts.

The preparation of dentifrice compositions is well known in the art. U.S. Pat. Nos. 3,996,863, 3,980,767, 4,328,205 and 4,358,437, which are incorporated herein by reference, describe toothpastes and methods of production thereof which may be utilized for production of the dentifrices of the present invention.

The following example is illustrative of the subject invention, and does not limit it. All parts or percentages are by weight and all temperatures are in degrees C, unless specifically stated to be otherwise.

EXAMPLE I

Calcium acetate was encapsulated in an ethyl cellulose matrix by adding a mixture of 300 parts ethyl cellulose, 700 parts calcium acetate and 1000 parts of ethyl alcohol to a Ross mixer and agitated for 10 minutes to prepare a viscous paste which was then extruded as a flat sheet through the nip of a steam heated (107° C.) double drum dryer rotating at 1.56 ft./min. in a chamber sealed to the atmosphere. Vaporized solvent was removed by vacuum to a solvent recovery system. The dried sheet was passed into a Sweco mixed media grinder and pulverized to particles which were screened to a size of −30+100 mesh. Thereafter the pulverized particles were passed through a series of water baths heated to 65° C. and then dried at 150° C. to obtain dry encapsulated calcium acetate particles suitable for use in dentifrice compositions containing reactive fluoride salts.

Calcium ion analysis, by inductive coupling plasma, indicated that the washed and dried particles had less than 1% exposed soluble calcium indicating that the calcium acetate was encased in continuous surface coating of ethyl cellulose and that minimal exposed calcium was available to react with any fluoride ion present in dentifrice.

The encapsulated calcium acetate particles were incorporated in a dentifrice composition having the ingredients listed in Table I below.

TABLE I

| Ingredient | Weight % |
| --- | --- |
| Sorbitol (70%) | 60.77 |
| Polyethylene glycol 600 | 3.0 |
| Carboxymethyl cellulose | 0.60 |
| Sodium saccharin | 0.30 |
| Water, deionized | 6.51 |
| Zeodent 115 | 25.50 |
| Sodium fluoride | 0.243 (1100 ppm) |
| Flavor | 0.72 |
| Sodium lauryl sulfate | 1.2 |
| Encapsulated calcium acetate | 0.50 |
| Tetrasodium pyrophosphate | 0.5 |
| FDC Blue 1 (1% dye soln.) | 0.16 |

The dentifrice of Table I (designated "Example I Dentifrice) was packaged in sealed plastic toothpaste tubes and aged for six weeks at 50° C. in an air oven. Fluoride ion analysis of the aged dentifrice indicated 1050 ppm fluoride was present evidencing minimal fluoride ion loss from the dentifrice, the ethyl cellulose having remained substantially intact after processing and aging of the dentifrice.

The degree of fluoride uptake on hydroxapatite disks (chemically similar to tooth enamel) was determined for the Example I dentifrice and for comparative purposes, the same dentifrice was prepared and evaluated for fluoride uptake except that the encapsulated calcium acetate ingredient was not present, the comparative dentifrice being identified as Composition "C". A slurry (1:3 in water) of these dentifrices was brushed for 30 seconds in a trough. The brushed slurry was centrifuged and the supernatant collected. The hydroxyapatite (HAP) disks were exposed to the slurry for 5 minutes each time for a total of 10 exposures. The disks were then dipped into perchloric acid for 60 seconds to remove the surface layer containing the fluoride and then analyzed for fluoride ion content. The results are recorded in Table II below.

TABLE II

| Dentifrice Composition | % Ca Acetate Particles | Particle size (mesh) | Fluoride uptake on HAP disks (ppm) |
| --- | --- | --- | --- |
| Ex. 1 | 0.50 | −60 + 100 | 0.22 |
| Ex. 1 | 0.50 | −30 + 60 | 0.23 |
| C | — | — | 0.02 |

The results show that the disks that were exposed to the Example I dentifrice containing both encapsulated calcium acetate and sodium fluoride showed a substantial and significant (greater than 10 fold) increase in fluoride uptake as compared to the comparative dentifrice (C) which did not contain calcium acetate.

EXAMPLE II

In a series of aging tests the procedure of Example I was repeated except that for purposes of comparison, comparative encapsulating materials listed in Table III were used to prepare calcium acetate particles by spray drying rather than the solvent casting method of the present invention.

TABLE III

| Comparative Particle | Encapsulant Material |
| --- | --- |
| $C_1$ | Non-plasticized ethyl cellulose |
| $C_2$ | Vegetable wax |

The dentifrice composition of Example I as well as dentifrice compositions containing the comparative calcium acetate particles $C_1$ and $C_2$ were prepared following the procedure of Example I and were packaged in sealed plastic toothpaste tubes and aged at 120° F. for a six week period. The fluoride availability of the aged dentifrices is recorded in Table IV below.

TABLE IV

| Encapsulated Particle Used in Dentifrice Composition | Fluoride Availability (ppm) | | | |
| --- | --- | --- | --- | --- |
| | Initial 72° F. | 2 weeks | 4 weeks | 6 weeks |
| Example I | 1090 | 1085 | 1063 | 1050 |
| $C_1$ | 1085 | 953 | 467 | 208 |
| $C_2$ | 1000 | 695 | 210 | 55 |

The data recorded in Table IV show that over the 6 week aging period as contrasted with the encapsulated calcium acetate particles prepared by solvent casting, (Example I) in which there was no meaningful loss of fluoride availability in the dentifrice, substantially complete loss of fluoride availability was observed in dentifrices in which the encapsulant material was either non plasticized ethyl cellulose ($C_1$), or vegetable wax ($C_2$) both being prepared by a spray drying process.

What is claimed is:

1. A method for encapsulating a water soluble reactive agent in an alkyl cellulosic polymer matrix to provide an encapsulated product from which leaching of the reactive agent into an aqueous dentifrice containing a compound reactive with the encapsulated agent is substantially prevented, the method comprising the steps of (a) uniformly dispersing the reactive agent in an alkyl cellulosic polymer and a solvent for the polymer to form a paste;
(b) casting the paste onto a sheet forming substrate to form a sheet of reactive agent encased in the alkyl cellulose polymer;
(c) grinding and subdividing the sheet having the reactive agent encased therein into particles of a predetermined size;
(d) washing the particles with water to remove any encased agent exposed by the grinding; and
(e) drying the particles of encapsulated reactive agent.

2. The method of claim 1 wherein the alkyl cellulosic polymer is ethyl cellulose.

3. The method of claim 1 wherein the particle is comprised of about 40 to about 80% by weight of the water soluble reactive agent and about 20 to about 60% by weight of the alkyl cellulosic polymer.

4. The method of claim 1 wherein the encapsulated compound is a water soluble calcium salt and the reactive compound in the dentifrice is a fluoride salt.

5. The method of claim 4 wherein the calcium salt is calcium acetate.

6. The method of claim 1 wherein the particles have a size of −30 to +100 mesh.

* * * * *